(12) United States Patent
Sotereanos

(10) Patent No.: US 6,284,002 B1
(45) Date of Patent: Sep. 4, 2001

(54) PROXIMAL FEMORAL REPLACEMENT IMPLANT AND METHOD OF IMPLANTING THE SAME

(76) Inventor: Nicholas G. Sotereanos, 2335 Buena Vista Dr., McKeesport, PA (US) 15135

(*) Notice: Subject to any disclaimer, the term of this patent is extended or adjusted under 35 U.S.C. 154(b) by 0 days.

(21) Appl. No.: 09/321,332

(22) Filed: May 27, 1999

(51) Int. Cl.[7] .................................................. A61F 2/32
(52) U.S. Cl. .................................................. 623/27; 623/11
(58) Field of Search ..................... 623/23.11, 23.12, 623/23.13, 23.14, 23.15, 23.43, 23.44, 23.27

(56) References Cited

U.S. PATENT DOCUMENTS

| | | | |
|---|---|---|---|
| 2,718,228 | * | 9/1955 | Van Steenbrugghe ............ 623/23.14 |
| 4,834,756 | * | 5/1989 | Kenna .................... 623/23.6 |
| 5,593,451 | | 1/1997 | Averill et al. . |

FOREIGN PATENT DOCUMENTS

| | | | |
|---|---|---|---|
| G 91 03 574.0 | | 4/1992 | (DE) . |
| 299 21 577 U1 | | 2/2000 | (DE) . |
| 200 07 950 U1 | | 7/2000 | (DE) . |
| 0457222 | * | 11/1991 | (EP) ...................................... 623/23 |
| 0 567 349 A1 | | 10/1993 | (EP) . |
| 1047640 | | 12/1953 | (FR) . |
| 1122634 | | 9/1956 | (FR) . |
| 80495 | * | 3/1963 | (FR) ...................................... 623/23 |
| 2689390 | | 10/1993 | (FR) . |
| 2697996 | * | 5/1994 | (FR) ...................................... 623/23 |
| WO 86/03962 | | 7/1986 | (WO) . |
| 093016663 | * | 9/1993 | (WO) ...................................... 623/23 |
| WO 97/25939 | | 7/1997 | (WO) . |

* cited by examiner

*Primary Examiner*—David J. Isabella
(74) *Attorney, Agent, or Firm*—Kirkpatrick & Lockhart LLP

(57) ABSTRACT

An implant and method for replacement of the proximal portion of a femur, and specifically for replacement of the natural femoral head is provided. The implant includes a body member for insertion, in use, through the natural femoral neck and in substantial alignment therewith, a head member with a spherical portion for engagement with a natural or a prosthetic hip socket, and an optional sleeve for altering the position of the spherical portion of the head member relative to the body member. The body member may also include a collar designed to rest on the resected surface of the remaining intact natural femoral neck. A member for joining the head member to the body member is further provided which may integrally join the head and body members or, where the implant is comprised of modular components, the joining member may be in the form of a protrusion or a recess on the body member for engaging a complementary recess or protrusion, respectively, on the head member. The method for implanting the femoral head includes rotating a cutting portion of a reamer into engagement with the lateral side of the femur and along the axis of the femoral neck, morselizing the natural femoral neck with a reamer, and inserting the implant into the passage at the lateral side of the femur.

27 Claims, 11 Drawing Sheets

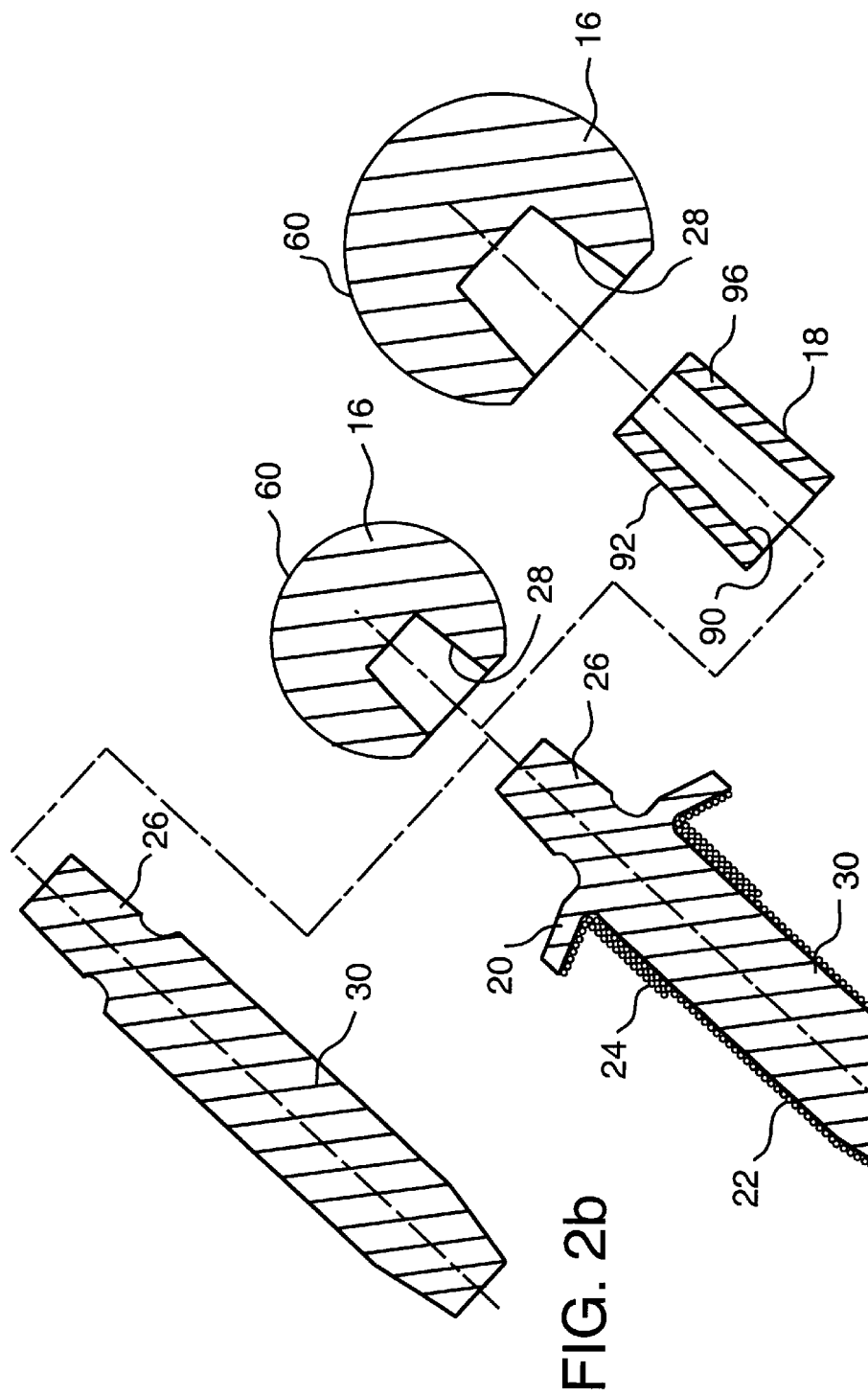

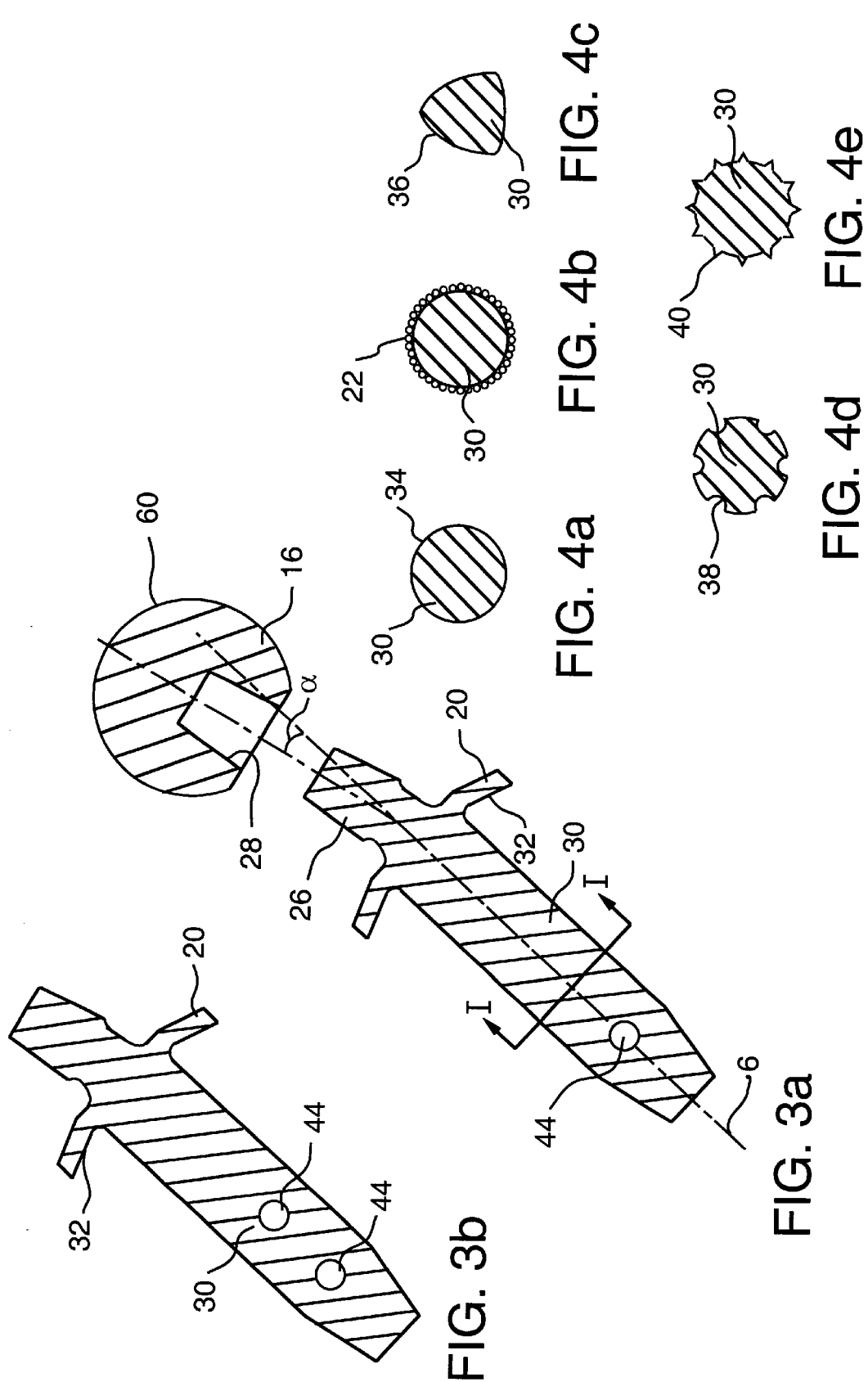

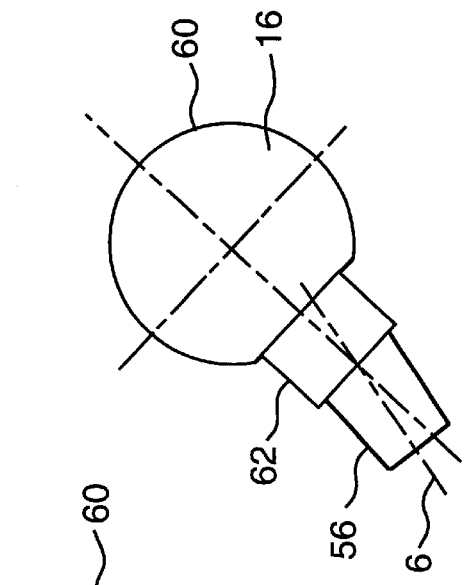
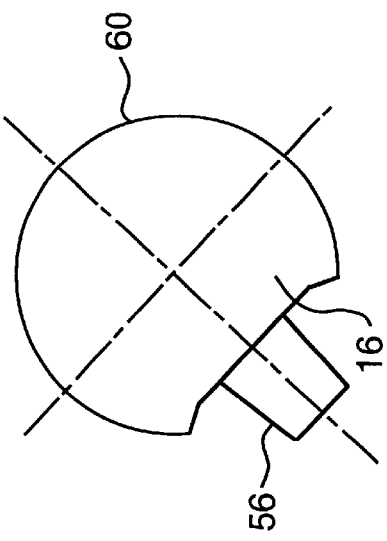
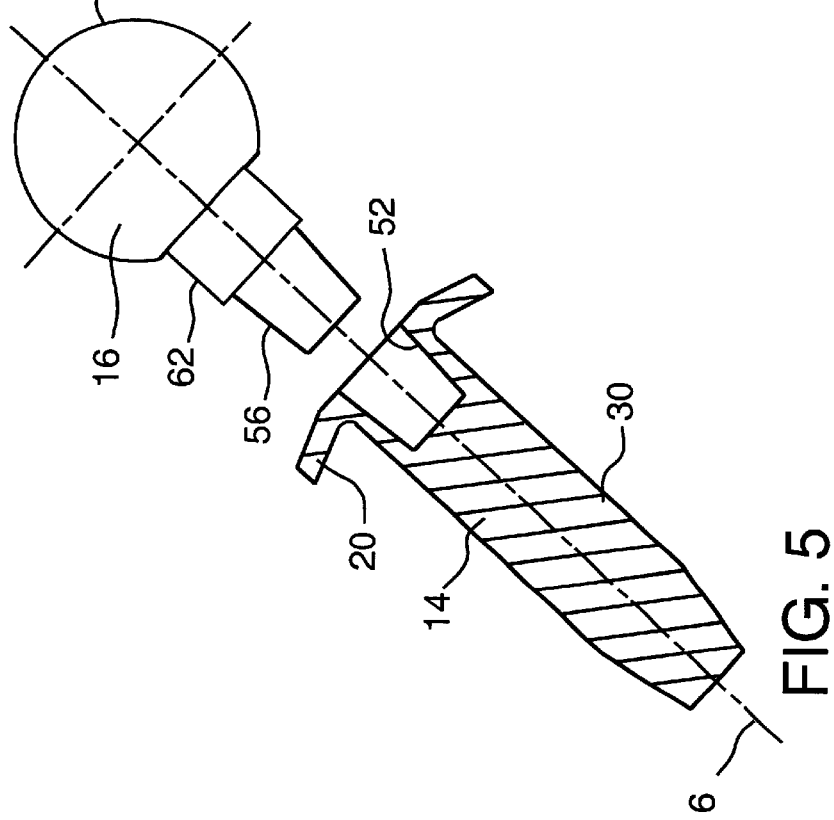
FIG. 6a
FIG. 6b
FIG. 5

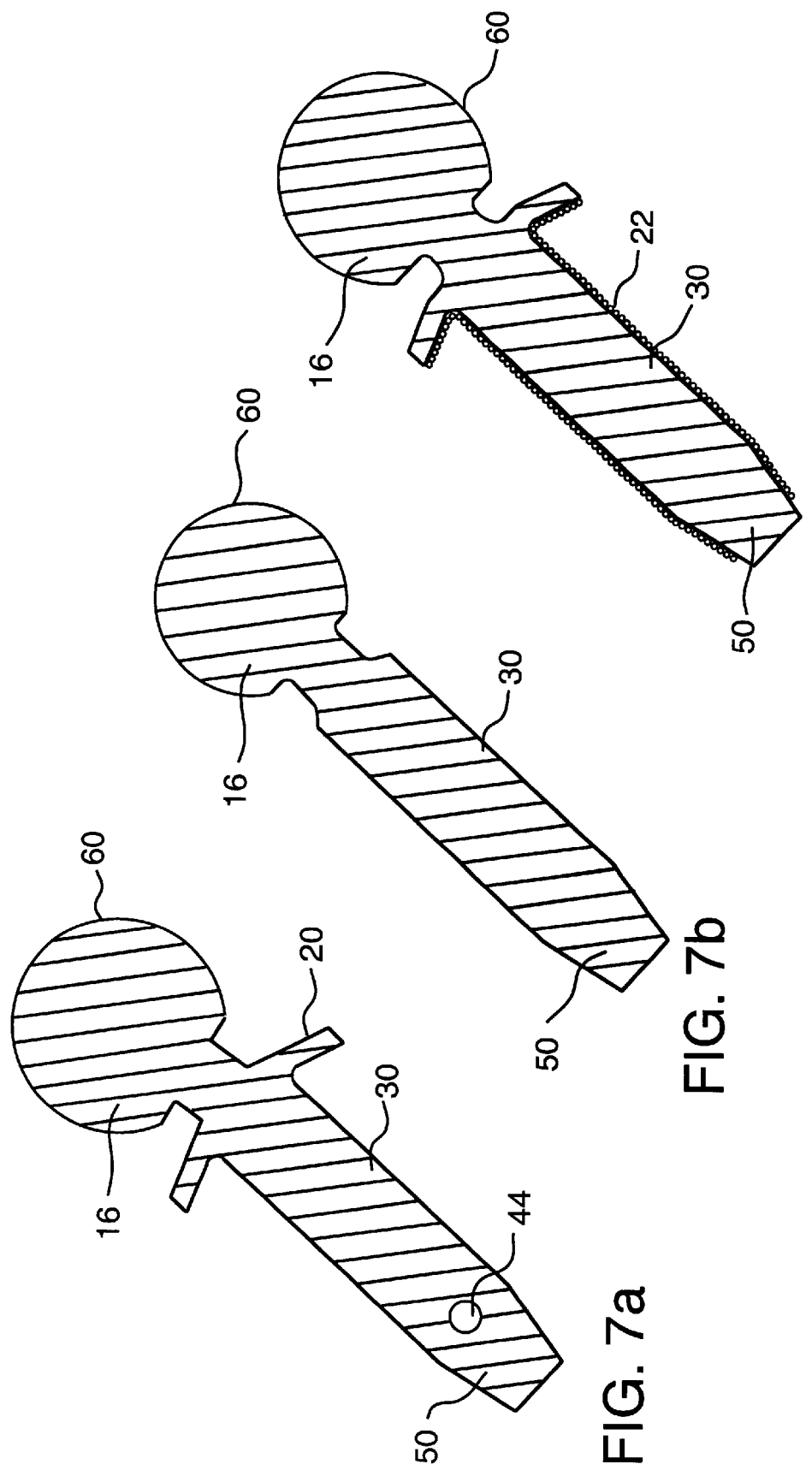

PROXIMAL FEMORAL REPLACEMENT IMPLANT AND METHOD OF IMPLANTING THE SAME

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The subject invention relates to femoral implants, and, more particularly, to a modular proximal femoral implant for replacing a femoral head and the method of implanting the same.

2. Description of the Invention Background

A widely used design for replacement of the proximal portion of a femur employs an elongate, often curved, shaft that extends into the medullary canal of the femur. This design has the tendency to place unnatural stresses on the femur which lead to pain and the consequent curtailment of activity for the patient. The useful life of an intramedullary implant is often less than the expected life span of a young patient.

Previously known prostheses for replacing a femoral head that do not extend into the medullary canal have been mechanically complex or have proven troublesome in actual use. Huggler, U.S. Pat. No. 4,129,903 and Grimes, U.S. Pat. No. 4,795,473 are examples of prosthetic implants having a side plate attached to the exterior lateral side of the femur opposite the femoral head. Screws are used to secure the plate to the femur and one or more holes are drilled into the femur for securing the plate to the bone. The additional holes and the stresses at the site of fixation are believed to cause trauma to the bone.

Masini, U.S. Pat. No. 5,571,203 discloses a device having a shaft that extends through a resected portion of the proximal femur, positioned co-axially relative to the longitudinal axis of the femur. The device is secured by a screw or similar locking device that extends into the femur from the lateral side, just below the greater trochanter. It is believed that the natural forces applied to the prosthesis during normal hip motion result in the application of shear forces to the greater trochanter. The shear forces can be harmful to the greater trochanter and can permit micromovement of the prosthesis on the unsecured side.

A conventional method for implanting the above types of femoral head implants is described in *Campbell's Operative Orthopaedics*, (Mosby, 7th ed., 1987) and typically includes making a large incision in the patient's lateral side at the hip joint and through the skin and muscle, dislocating the hip and then sawing off the femoral head. This method is considered invasive because of the need to dislocate the hip and cut through muscle surrounding the hip joint. Invasive procedures increase the trauma to the patient, the potential for complications, recovery time and the cost.

Replacement of the proximal portion of the femur is sometimes necessary due to degenerative bone disorders or trauma to otherwise healthy bone caused by accidental injury. In the latter instance it is desirable to replace the traumatized portion of the bone without causing further trauma to healthy bone. There is a need, therefore, for an implant that replaces a traumatized portion of the femur, but also significantly minimizes stress to the remaining healthy bone and that can be implanted by a method that is not invasive.

SUMMARY OF THE INVENTION

The present invention provides a proximal femoral replacement implant that both reduces trauma to the femur and the time required to perform the implantation. The design of the implant of the present invention transfers forces to the femur in a natural way and minimizes micromotion. The implant of the present invention includes a solid body member having a longitudinal axis, a distal end to receive a crosslocking fastener, and a proximal end. The body member is configured such that it is positioned in the natural femoral neck with passage of the distal end through the medial side of the femur, or through a reamer hole in the lateral side of the femur. The implant also includes a head member having a distal end and a proximal spherical portion configured for positioning in a natural or prosthetic hip socket, and a joining portion for joining the distal end of the head member to the proximal end of the body member.

The implant may also include a collar positioned at the proximal end of the body member and configured for abutting contact, in use, with a proximal surface of the resected femoral neck when the implant is inserted medially.

The body member is preferably configured in cross section to inhibit rotational motion following implantation. The body member may be triangular, fluted or scalloped in cross section. Alternatively, the body member may be circular in cross section.

At least one passage may be provided through at least a portion of the body member in a direction transverse to the longitudinal axis of the body member. At least one fastener for insertion, in use, through the greater trochanter and the passage in a direction towards the lesser trochanter of the femur without passing through the medial side of the femur may be provided to prevent rotational motion of the body member or to prevent the body member from backing out of the femur following implantation.

The body member and the head member may be integrally attached at the joining portion, but may also, and preferably, form modular components for complementary engagement with each other through joining portions. The joining portion preferably includes a first engagement portion and a second engagement portion, the first and second engagement portions being configured for complementary engagement with each other. The joining portion may extend outwardly from the body member at an acute angle relative to the longitudinal axis of the body member to provide anteversion. Alternatively, the joining portion may extend outwardly from the body member in substantial coaxial alignment with the longitudinal axis of the body member. The first engagement portion may be a recess formed either in the body member or the head member for receiving the second engagement portion and the second engagement portion may be a protrusion formed respectively, in the head member or the body member for insertion into the recess.

The modular embodiment of the implant of the present invention also preferably includes an optional member, preferably a sleeve, for altering the position of the spherical portion of the head member relative to the body member. The sleeve has an inner surface and an outer surface and defines a wall therebetween. It is mountable such that, in use, the inner surface slides over the protrusion and the outer surface is received within the recess. The sleeve may be longer in length than the protrusion of the joining portion for extending the distance between the spherical member and the body member. Additional sleeves may be provided wherein the wall has non-uniform, gradual thickness changes such that, in use, the central axis of the sleeve relative to the outer surface of the sleeve is at an acute angle to permit positioning of the head member at an angle relative to the longitudinal axis of the body member when needed.

The present invention further provides a method for implanting the proximal femoral replacement implant of the present invention using a reamer or burr which includes rotating the reamer into engagement with the lateral side of the femur and along the axis of the femoral neck to form a passage therethrough, morselizing the natural femoral head with the reamer or burr while keeping the natural femoral neck substantially intact, and inserting the femoral replacement implant into the passage from the lateral side of the femur.

Other details, objects and advantages of the present invention will become apparent with the following description of the present invention.

BRIEF DESCRIPTION OF THE DRAWINGS

For the purpose of illustrating the preferred embodiments and methods of implantation of the proximal femoral replacement implant of the present invention and not for limiting the same, reference is made to the drawings in which:

FIGS. 2a, b and c represent an exploded cross-sectional view of several components of the modular embodiment of the implant of the present invention;

FIGS. 3a and b are cross-sectional views of two embodiments of the implant of the present invention illustrating an anteverted member for mounting the femoral head member and one or more holes to accept cross-fastening devices;

FIGS. 4a–e illustrate cross-sectional views through the line I—I of FIG. 3(a) of the alternative embodiments of the shaft portion of the implant;

FIG. 5 is a view of an alternative embodiment of the body and head members of the implant of the present invention showing the mounting member as part of the head member;

FIGS. 6a and b illustrate two alternative modular head members, an anteverted head member and an enlarged head member;

FIGS. 7a–c are cross-sectional views of embodiments of the present invention, wherein the body member and the head member form a unitary implant;

DETAILED DESCRIPTION OF THE INVENTION

Figure 1:
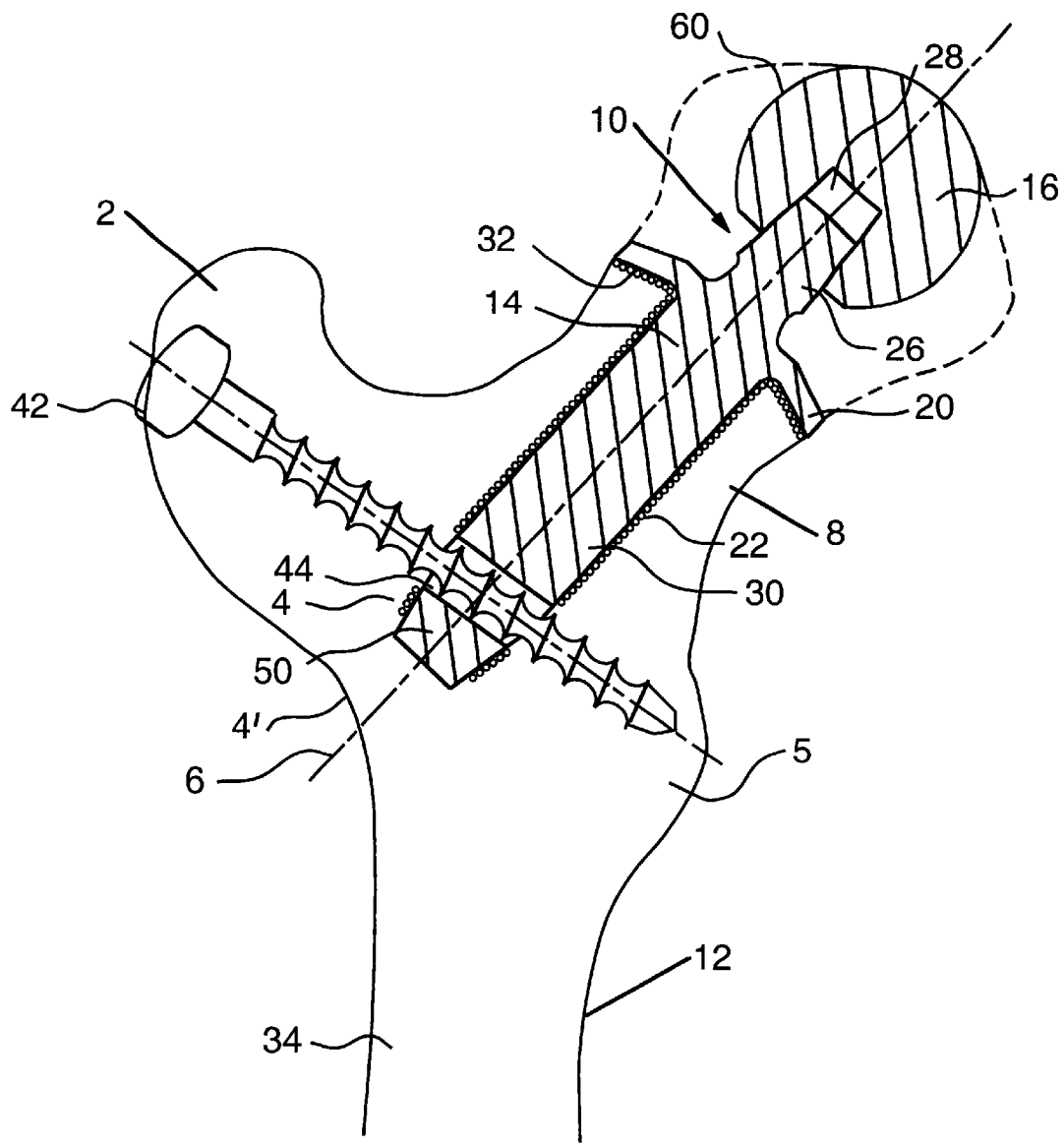
FIG. 1 is a cross-sectional view of an embodiment of the proximal femoral replacement implant of the present invention shown as implanted in a femur.

FIGS. 1 through 8 illustrate various embodiments of the proximal femoral replacement implant 10 of the present invention. Referring to FIG. 1, the modular embodiment of implant 10 is shown as it would appear after implantation in a femur 12. The natural femoral head, illustrated in hidden lines, has been removed, but the femoral neck 8 and the remainder of the femur 12 remain intact. The present invention is particularly suited for patients having good bone quality. The present invention is not believed to be suited to those patients having severely osteoporotic bone.

The modular embodiment of implant 10 includes generally a body member 14, a head member 16 and an optional member, such as sleeve 18 (FIGS. 2 and 8) for positioning the head member 16. One embodiment of the body member 14 is a solid unitary structure having a symmetrical elongate shaft 30 with a tapered distal end 50, an engagement surface, preferably in the form of a mount or neck 26 and a collar 20.

Referring to FIG. 1, the body member 14 is configured for insertion into the natural femoral neck 8 such that the underside 32 of the collar 20 rests on the resected surface of remaining intact femoral neck 8 and the central longitudinal axis 6 of the shaft 30 is preferably generally in coaxial alignment with the central longitudinal axis of the femoral neck 8. Although some deviation from alignment with the neck axis can be tolerated and would in practice be determined by the surgeon in each case, the axis 6 of shaft 30 preferably extends along the axis of the femoral neck 8 into the extramedullary area 4 in the portion of the femur intermediate the greater and lesser trochanters 2 and 5. The shaft 30 does not extend into the medullary canal 34 and the end 50 of shaft 30 does not extend through to the exterior of the femur on the lateral side. The entire implant is designed to be positioned only in the proximal portion of the femur. The implant 10 of the present invention thereby avoids two significant causes of stress on the healthy bone of an implant patient.

The collar 20 also aids in properly distributing the forces applied to the femur 12. The force of the patient's weight is distributed by the collar 20 over the resected surface on which the collar 20 rests. The collar 20 may be flat, angled or curved in configuration. The resected surface is preferably cut to match the configuration of the collar 20 so that the collar 20 contacts substantially all of the resected surface of the femur 12. Alternatively, there may be no collar 20. An embodiment of the body member 14 having no collar 20 is shown in FIG. 2b.

The shaft 30 may be made in a variety of cross-sectional configurations. Referring to FIGS. 4a–e, examples include circular 34 (FIG. 4a), circular with beads or another bone ingrowth enhancing surface (FIG. 4b), triangular 36 to complement the cross-sectional shape of the natural femoral neck 8 (FIG. 4c), scalloped 38 (FIG. 4d), and fluted 40 (FIG. 4e). Those skilled in the art will appreciate that a number of cross-sectional configurations may be employed. The triangular 36, scalloped 38 and fluted 40 cross-sectional configurations restrict rotational movement of the shaft 30 after implantation until bone ingrowth progresses enough to secure the implant 10 in position.

Alternatively, one, two or more fasteners such as cross nails, screws or other securing members 42 (FIG. 1) can be used to prevent rotation and to further secure the body member 14 from backing out of the femur 12 after implantation. When cross fastening is desired, shaft 30 includes one or more transverse holes 44 for receiving securing members 42. See FIG. 3. When used, the securing members 42 extend through the femur 12 from the greater trochanter 2 in the direction of the lesser trochanter 5, but do not extend through the medial side of the femur 12. Where cross-fastening is employed, it may be beneficial to remove the securing members 42 at a later time. Such removal may be desirable, for example, where cross-fastening is needed only for a short time to prevent movement until bone ingrowth has occurred. Alternately, if the age or activity level of the patient or the condition of the femur 12 or other secondary consideration warrants cross-fastening, the use of securing members 42 can be planned from the outset of surgery.

In many circumstances, however, the need for cross-fastening may not be known until after implantation of the body member 14 is completed. In such a case, the embodiment of implant 10 having one or more holes 44 will be used. After implantation, force may be applied to the body member 14 to determine whether rotation or loosening is likely. If it appears that rotation or loosening is unlikely, cross-fastening may be avoided. If, however, it appears that rotation or loosening is likely, the surgeon may, at that time, utilize one or more securing members 42 to prevent such undesirable movement of the implant 10.

In the embodiment, shown in FIG. 1, at least a portion of the surface of shaft 30 and the underside 32 of the collar 20 have a porous coating 22 to promote bone ingrowth. A most preferred surface coating is made of at least one layer of sintered beads, preferably titanium, cobalt or some other bio-compatible material. Other suitable coating materials may be used such as hypoxy or hydroxy appetite. A second layer of beads 24 over the portion of shaft 30 adjacent collar 20 provides additional surface area for bone ingrowth. See FIG. 2a. Multiple layers of beads further inhibit rotation and minimize micro-motion of the implant 10 in the femur 12. Micro-motion is harmful because it wears the inner surface of the bone where it contacts the implant 10, loosening the shaft 30 and thereby increasing the potential for the prosthesis to rotate in the femur 12 or lift out of the femur 12. For example, two layers of beads 22 and 24 or other coating material may be positioned on the proximal portion of the shaft 30 where the risk of wear on the femur 12 has been observed to be the greatest. Bone ingrowth can also be enhanced by varying the size of the beads to create different pore sizes. As an alternative to metal beads, the coating may be a plasma sprayed coating or the surface of shaft 30 may be roughened by any suitable known grit blasting process.

The body member 14 is preferably from about 50 mm to 120 mm in length and from about 12 mm to 30 mm in diameter. For adult female patients, the natural femoral neck 8 varies in diameter from about 14 mm to 22 mm. For adult male patients, the natural femoral neck 8 varies from about 16 mm to 34 mm in diameter. The length and diameter of the shaft 30 of body member 14 will necessarily be less than the diameter of the proximal femur 12 and the natural femoral neck 8 in which the implant 10 is positioned. In certain circumstances, the implant 10 may be suited for implantation in children. The variations in sizes of the implant 10 will fall within the anatomical ranges and constraints of the patient population. In order to accommodate patient differences, the various modular components of the implant 10 of the present invention can be made in a variety of sizes interchangeable with other components.

The body member 14 also includes an engagement surface at its proximal end adapted for complementary engagement with an engagement surface on the distal end of the head member 16 for securely joining the two components together. A preferred surface that is provided is a protrusion, like that of mount 26, which is preferably tapered for sliding insertion into a complementary recess 28 in the head member 16 for securing the two components together. See FIG. 1. Alternatively, the body member 14 may include a recess 52 for receiving a protrusion, like that of mount 56 on head member 16. See FIG. 5.

The head member 16 includes a generally spherically shaped portion 60 and an engagement surface in the form of the recess 28 (FIGS. 2 and 3) for complementary engagement with the engagement surface of body member 14 which is mount 26. Alternatively, the engagement surface of the head member 16 may be mount 56 (FIGS. 5 and 6) which is inserted into the engagement surface of the body member 14, recess 52. In those embodiments of head member 16 having a mount 56, an annular portion 62 may be positioned between the spherical portion 60 and mount 56. See FIGS. 5 and 6a. The head member 16 extends from the body member 14 at a distance and angle above the collar 20 suitable to permit the spherical portion 60 to mate with the patient's hip socket (not shown). The degree of extension or angulation will match the anatomy of the particular patient. Like the body member 14, the head member 16 can be made in a variety of sizes to accommodate patient needs. A head member 16 having an enlarged spherical portion 60 is shown in FIG. 2c and in FIG. 6b.

Figure 8:
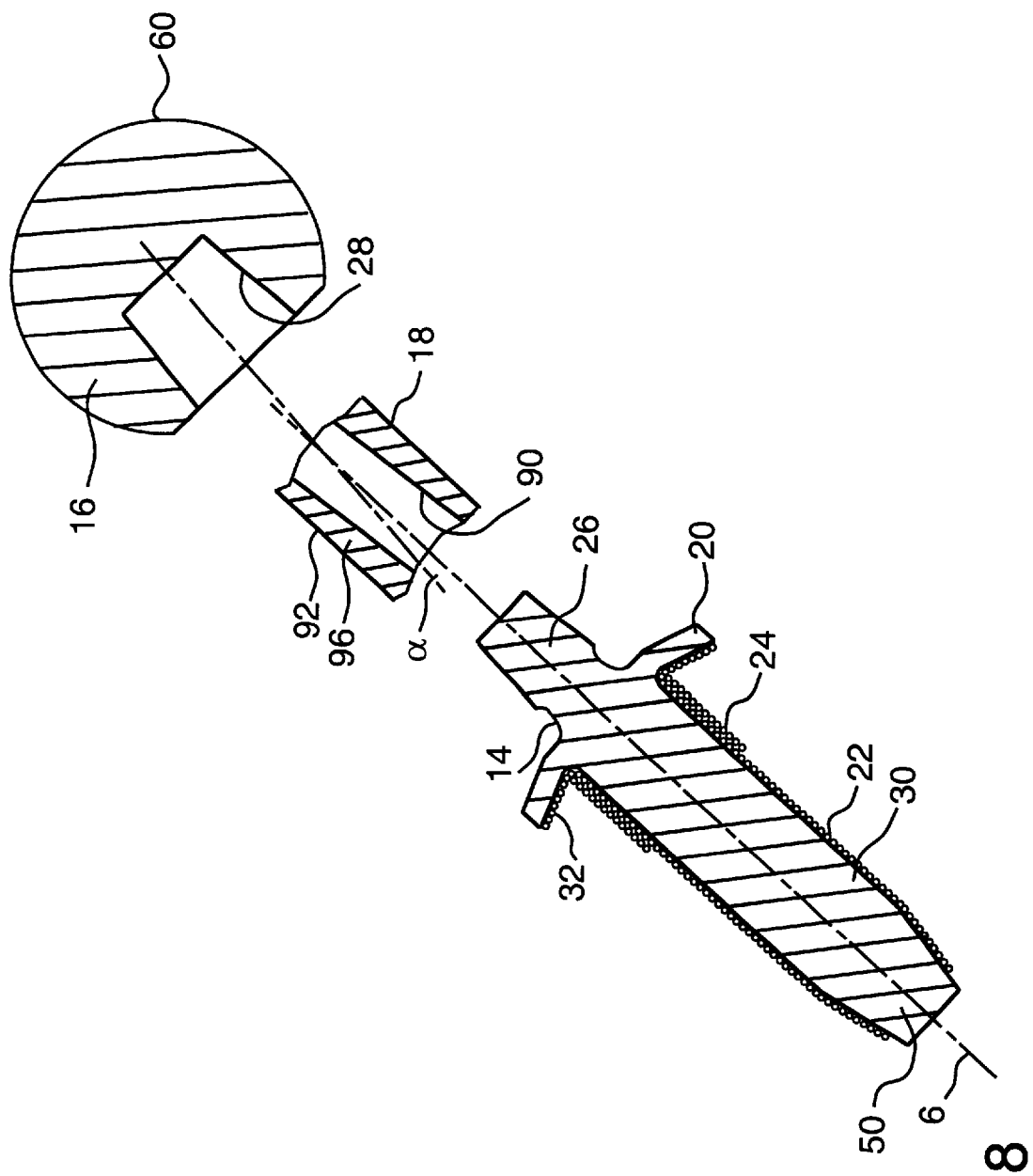
FIG. 8 is a cross-sectional view of an alternative embodiment of the proximal femoral implant of the present invention showing a sleeve member for introducing anteversion.
Figure 10:
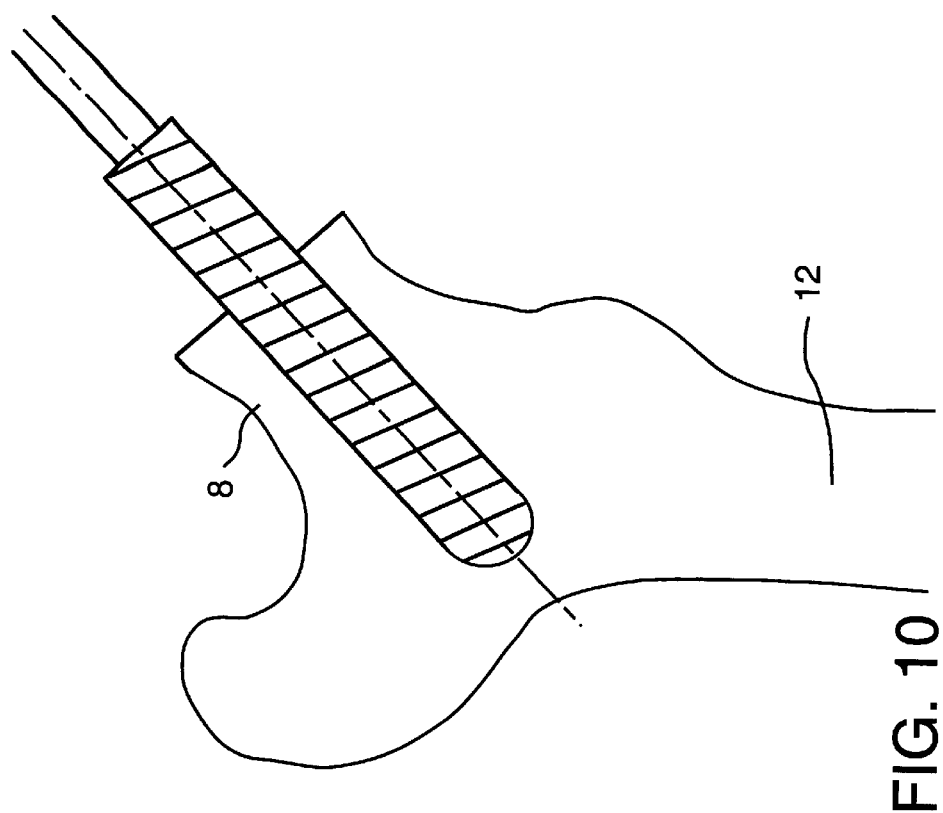
FIGS. 9–14 illustrate schematically the procedure for removal of the femoral head and the implantation of the proximal femoral implant of the present invention.

Referring to FIG. 2c and FIG. 8, an optional member, such as sleeve 18 for positioning the spherical portion 60 of the head member 16 is shown. Sleeve 18 slides over the mount 26 to increase the length or width of mount 26 (FIG. 2c), or to alter the angle at which the head member 16 extends from the body member 14, if anteversion is desired (FIG. 8). As shown in FIG. 8, sleeve 18 has an inner surface 90 and an outer surface 92 defining a wall 96 therebetween. The wall 96 thickness can vary gradually to position the head member 16 at an acute angle relative to the longitudinal axis 6 of the body member 14.

The head and body members 16 and 14 of the embodiment of the implant 10 of the present invention, shown in FIGS. 1 and 2, are in axial alignment with each other. However, several embodiments of implant 10 are configured for providing anteversion to permit the spherical portion 60 of head member 16 to mate with the patient's hip socket at an angle relative to the longitudinal axis of the shaft 30. Referring to FIGS. 3a and 3b, the mount 26 may extend at an angle from the central axis of the shaft 30. When the head member 16 is positioned on the mount 26, the head member 16 will be angled relative to the longitudinal axis of the shaft 30. Referring to FIG. 6a, the embodiment of head member 16 having a mount 56 may be configured such that the central axes of the spherical portion 60 and the annular portion 62 form an acute angle relative to the axis of the mount 56 and the body member 14 when the components are joined. In yet another embodiment, the anteversion may be achieved by angulation of recess 28 in head member 16.

Alternatively, implant 10 may be formed as a unitary structure as shown in FIGS. 7a, 7b, and 7c having integrally attached portions joining the head and body members 16 and 14. Embodiments with and without a collar 20, a hole 44, a porous coating 22 and anteversion (FIG. 7a) are provided.

Any bio-compatible material may be employed for the materials of the present invention. Suitable materials include, but are not limited to, stainless steel, titanium and cobalt. Any bio-compatible textures or coatings that engage the bone or that promote bone ingrowth may be utilized with the present invention.

Figure 9:
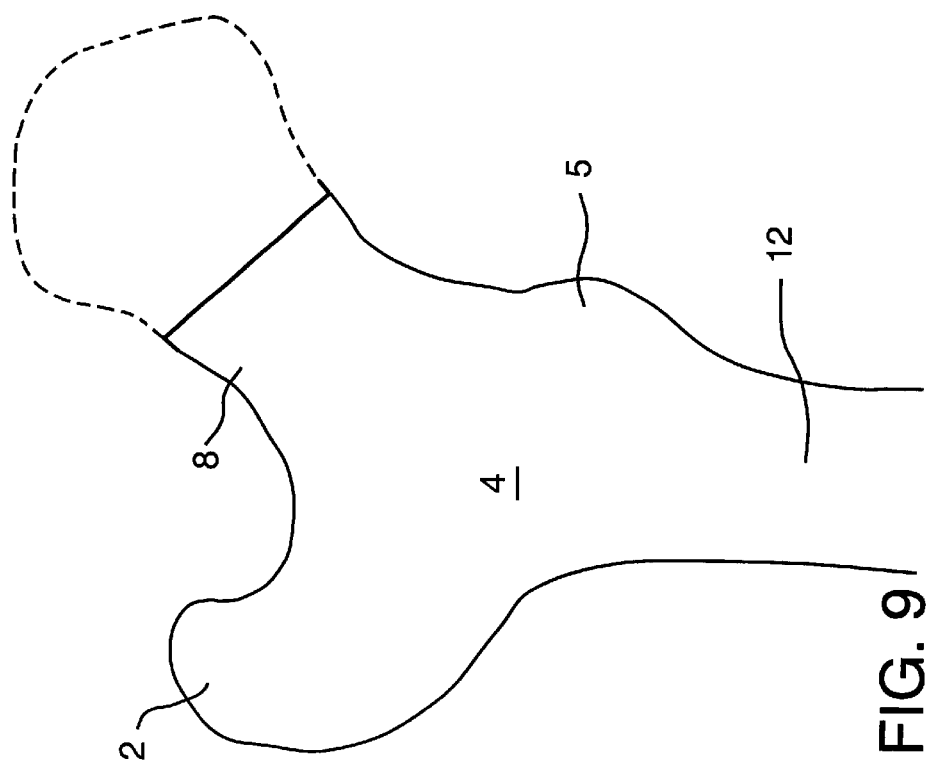
Figure 12:
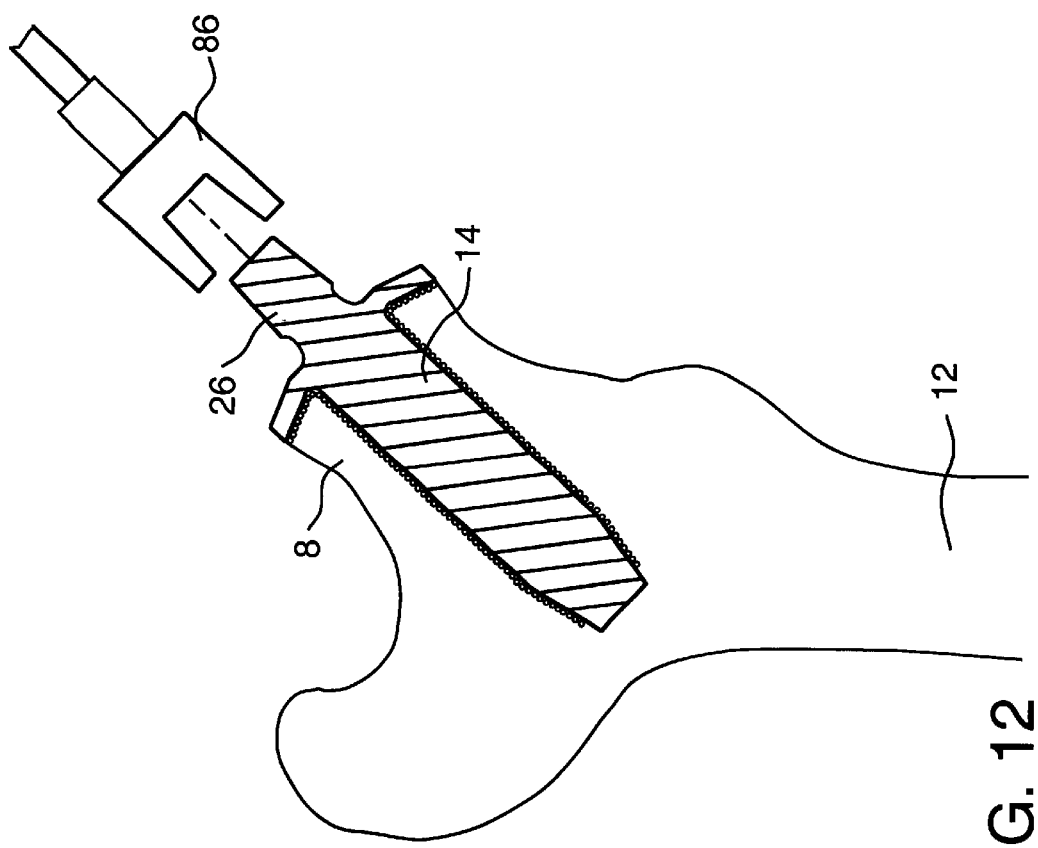
Figure 11:
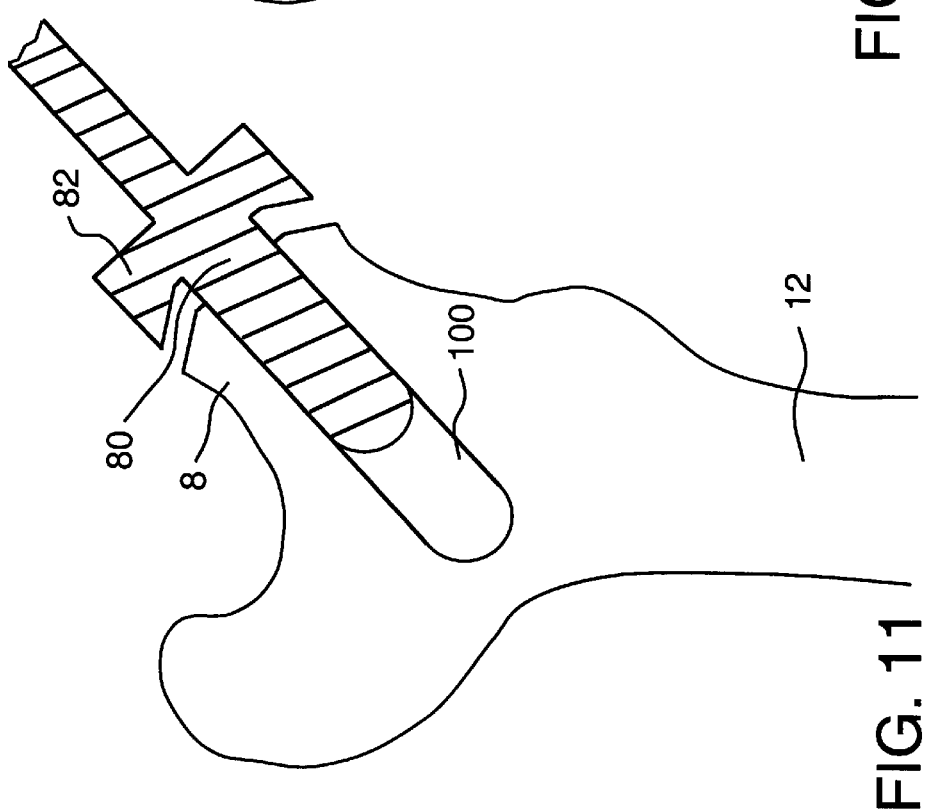
Figure 14:
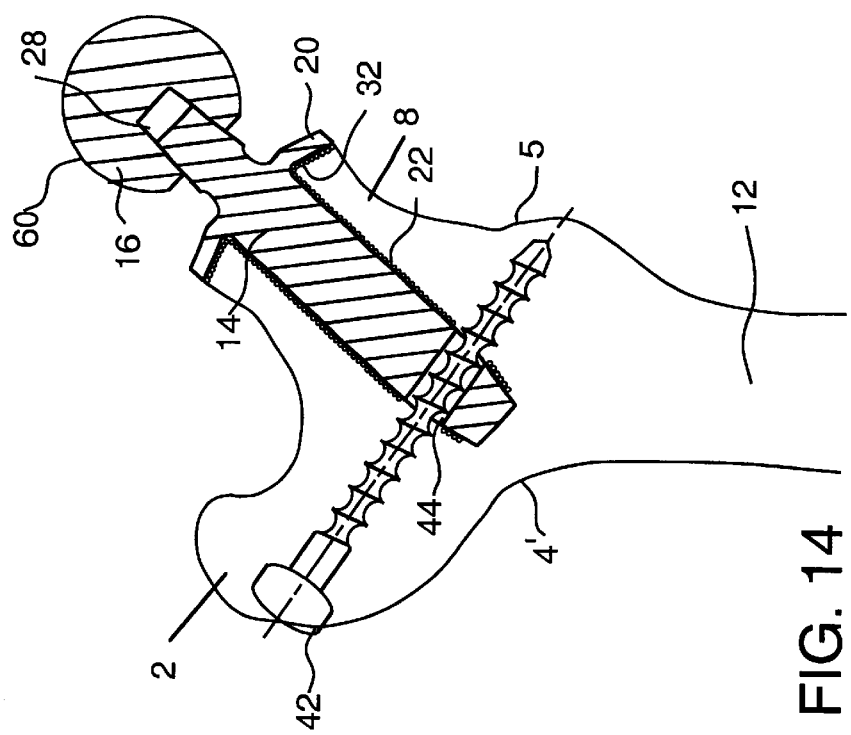
Figure 13:
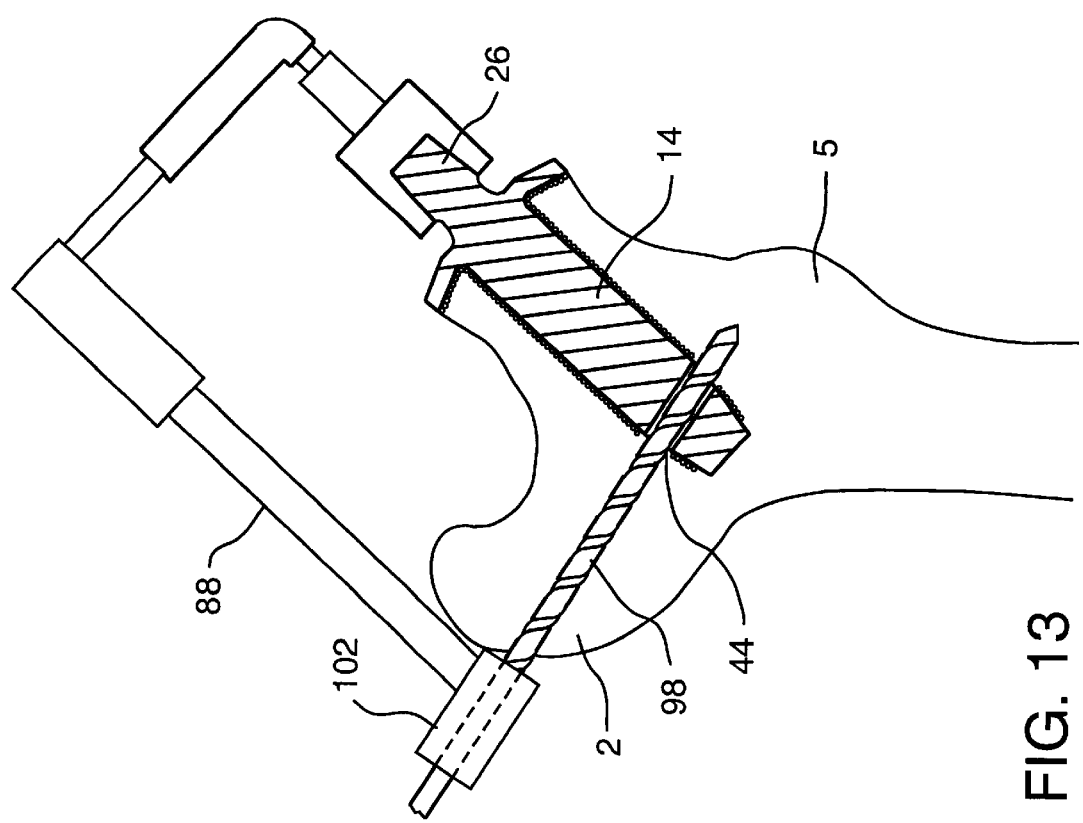

FIGS. 9–14 illustrate one method of implanting the implant 10 in a femur 12. An incision can be made along the lateral side at the hip of the patient. The muscle surrounding the hip is then separated and the hip is dislocated. The natural femoral head (illustrated in hidden lines) is then removed by, for example, sawing the femur 12 such that the femur 12 is left intact up to and including most or all of the femoral neck 8, as illustrated in FIG. 9. A canal 100 is then reamed to receive the shaft of a guide pin 80. If a body member 14 having a collar 20 is to be used, the resected surface of the remaining intact femoral neck 8 is finished to allow the collar 82 of the guide pin 80, and thus, the collar 20 of body member 14, to seat securely on the resected surface, as illustrated in FIG. 11, wherein the collar 20 of the implant 10 and the collar of the guide pin 80 have corresponding shapes. The guide pin 80 is removed and the implant 10 is then fit into the reamed canal 100, as illustrated in FIG. 12. The body member 14 is then pressed into the femur 12 using an impactor (not shown) as needed. A torque limiting wrench 86 may then be attached to the tapered mount 26 (or recess 52 as appropriate) of body member 14 and an amount of force, corresponding to physiologic loading levels, may be applied to verify the stability of the body member 14, as illustrated in FIG. 12. If there is motion at the interface of the implant 10 and the femur 12, a fastener, such as securing member 42, preferably in the form of a transverse locking screw, may be used for additional fixation. If the implant 10 is stable, the transverse fastener 42 may be omitted.

Where a transverse fastener 42 is used, as illustrated in FIGS. 13 and 14, a targeting guide 88 is fitted to the tapered mount 26 and aligned for use as a drill guide. A drill bit 98 may then be inserted through the drill bushing 102 of the targeting guide 88 and used to drill through the greater trochanter 2 of the femur 12, passing through the transverse hole 44 in the shaft 30 of the body member 14 and extending towards the lesser trochanter 5 at the medial cortical wall. A transverse fastener 42 of appropriate length is then inserted and tightened.

The head member 16 is then impacted onto the mount 26 of body member 14. If an extension in length or width or a change in angle is desired, a suitable embodiment of the optional sleeve 18 may be placed over the mount 26 prior to placement of the head member 16 onto the body member 14.

Figure 15:
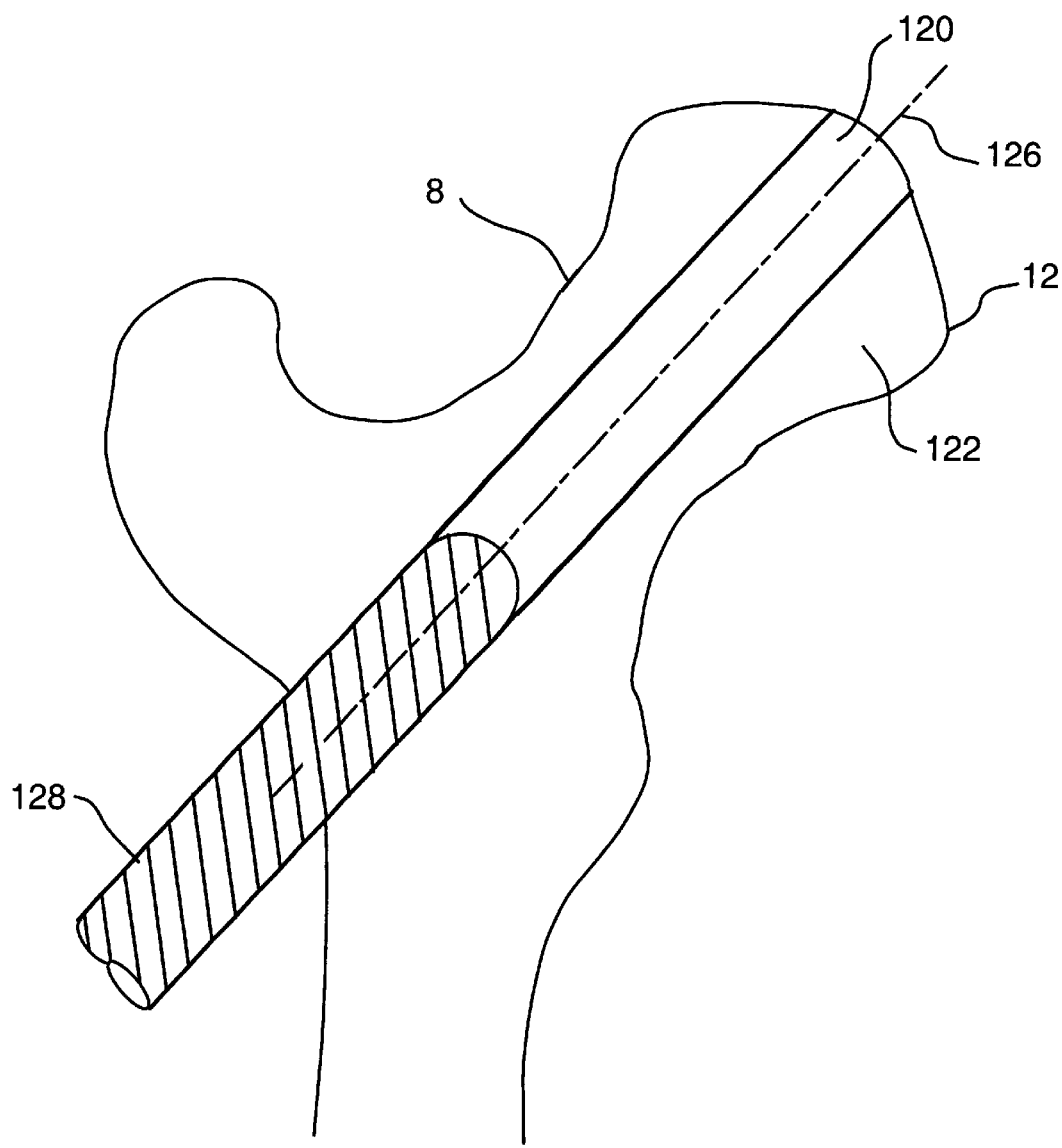
FIGS. 15 and 16 illustrate an alternative method for implanting the proximal femoral implant of the present invention.
Figure 16:
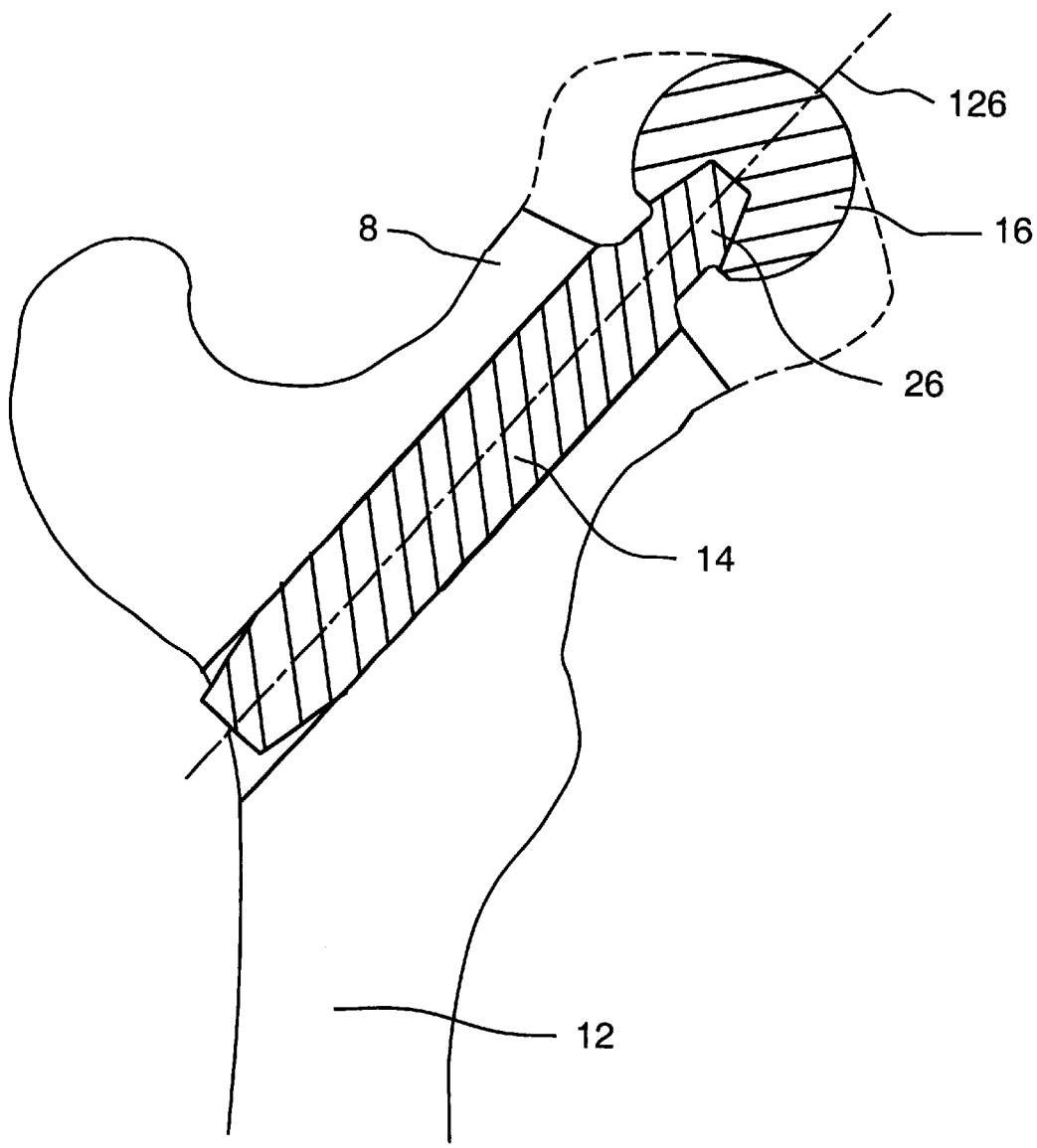

FIGS. 15 and 16 illustrate an alternative method of implanting the proximal femoral implant 10 of the present invention into the patient, which is less invasive than conventional methods. FIG. 15 is a cross-sectional view of the femur 12 with a passage 120 that is substantially co-axially aligned with the axis 126 of the femoral neck 8. FIG. 16 illustrates the proximal femoral implant 10 of the present invention, shown in FIG. 2b, implanted within the femur 12.

First, an incision at the lateral side of the hip is made of a size such that a reamer or burr 128 can be inserted into the patient and engage the femur 12 at the lateral side thereof and along the longitudinal axis 126 of the femoral neck 8. The size of this incision is substantially smaller than the incision made when the hip must be dislocated to sever the femoral head, as is the case with conventional methods of implantation. The reamer or burr 128 then reams a substantially cylindrical passage 120 through the femur 12 along the axis 126.

Alternatively, a series of reamers or burrs 128 can be used to achieve the desired diameter of the passage 120. A first reamer reams a passage 120 along the axis 126 of the femoral neck 8, then a second reamer having a larger diameter than the first reamer enlarges the diameter of the passage 120. The number of reamers used is dependent on the patient and the desired size of the passage 120. By enlarging the diameter of the passage incrementally, less damage is done to the femur 12.

The femoral head 122 is then morselized using an instrument positioned within the passage such as a reamer or burr. The small pieces of the femoral head 122 are then suctioned from the patient's hip and the surface of the resected femoral neck is shaped as desired.

In the case where it is necessary to reshape the natural acetabular cup (not shown) to correspond with the shape of the head member 16, a reamer having a collapsible cutting portion can be inserted through the passage 120 with the reamer in its collapsed position and opened when the collapsible cutting portion extends through the passage 120 at the medial side of the femur 12. The rotating cutting portion of the reamer is then brought into engagement with the natural acetabular cup to shape the cup to correspond with the shape of the head member 16.

In the case where the acetabular cup needs to be replaced, a small incision at the medial side of the hip must be made to insert the acetabular cup implant. The acetabular cup implant can be attached to the patient by any conventional method.

Once the acetabular cup is prepared, the body member 14 of the implant 10, shown in FIG. 2b, is inserted into the passage 120 using an impactor (not shown) such that the body member 14 is press-fitted within the femur 12 and the mount 26 is positioned such that it extends above the femoral neck 8. A torque limiting wrench (not shown) may then be attached to the tapered mount 26 of the body member 14 and an amount of force, corresponding to the physiologic loading levels, may be applied to verify the stability of the body member 14. If there is motion at the interface of the implant 10 and the femur 12, a transverse fastener 42 may be used, as discussed above. If an incision has not already been made to insert an acetabular cup implant, as noted above, a small incision must be made at the medial side of the hip and the head member 16 must be joined with the body member 14 at the mount 26.

Because the hip does not have to be dislocated and large incisions through muscle and tissue be made to implant the implant 10 of the present invention, the method of implantation of the present invention is a less invasive than the conventional methods.

Implant 10 of the present invention thus, solves many of the problems encountered by prior femoral head replacement prostheses. Those of ordinary skill in the art will appreciate that various changes in the details, methods, materials and arrangement of parts which have been herein described and illustrated in order to explain the nature of the invention may be made by the skilled artisan within the principle and scope of the invention as expressed in the appended claims.

What is claimed is:

1. An implant for replacing the proximal portion of a femur having a substantially intact natural femoral neck, medial side, lateral side, greater trochanter and lesser trochanter, the implant comprising:

a solid body member having a longitudinal axis, a distal end, a proximal end and at least one passage through the body member in a direction transverse to the longitudinal axis of the body member, and being configured for positioning, in use, in the natural femoral neck;

a head member having a distal end and a proximal spherical portion configured for positioning in a natural or prosthetic hip socket;

a joining portion positioned between the distal end of the head member and the proximal end of the body member; and at least one fastener for insertion, in use, through the greater trochanter and the passage of the body member in a direction towards the lesser trochanter of the femur without passing therethrough.

2. The implant recited in claim 1, wherein the solid body member has a length for positioning, in use, in the natural femoral neck without passage of the distal end through the lateral side of the femur.

3. The implant recited in claim 1 further comprising a collar positioned at the proximal end of the body member and configured for abutting contact, in use, with a proximal surface of the resected femoral neck.

4. The implant recited in claim 1 wherein the body member and the head member are integrally attached at the joining portion.

5. The implant recited in claim 4 wherein the joining portion extends outwardly from the body member at an acute angle relative to the longitudinal axis of the body member.

6. The implant recited in claim 4 wherein the joining portion extends outwardly from the body member in substantial coaxial alignment relative to the longitudinal axis of the body member.

7. The implant recited in claim 4 further comprising a collar positioned at the proximal end of the body member and configured for abutting contact, in use, with a proximal surface of the resected femoral neck.

8. The implant recited in claim 1 wherein the body member and the head member are separable modular components.

9. The implant recited in claim 8 wherein the joining portion comprises a first engagement portion and a second engagement portion, said engagement portions being configured for complementary engagement with each other.

10. The implant recited in claim 9 wherein the first engagement portion is a recess for receiving the second engagement portion and the second engagement portion comprises a protrusion configured for insertion into the recess.

11. The implant recited in claim 10 wherein the protrusion has an axis which, in use, is at an acute angle relative to the longitudinal axis of the body member.

12. The implant recited in claim 10 wherein the protrusion has an axis which, in use, is in substantial co-axial alignment to the longitudinal axis of the body member.

13. The implant recited in claim 10 wherein the protrusion extends from the distal end of the head member and the recess is within the proximal end of the body member.

14. The implant recited in claim 10 wherein the recess is within the distal end of the head member and the protrusion extends from the proximal end of the body member.

15. The implant recited in claim 10 further comprising an optional sleeve for altering the position of the spherical portion of the head member relative to the body member.

16. The implant recited in claim 15 wherein the sleeve is longer than the protrusion for extending the distance between the spherical portion and the body member.

17. The implant recited in claim 15 wherein the sleeve has an inner surface and an outer surface and is mountable, in use, such that the inner surface slides over the protrusion and the outer surface is received within the recess.

18. The implant recited in claim 17 wherein the sleeve defines a wall between the inner surface and the outer surface, the wall having non-uniform, gradual thickness changes such that, in use, the central axis of the sleeve is at an acute angle relative to the longitudinal axis of the body member.

19. The implant recited in claim 8 further comprising a collar positioned at the proximal end of the body member and configured for abutting contact, in use, with a proximal surface of the resected femoral neck.

20. The implant recited in claim 1 further comprising a first surface coating on at least a portion of the body member for promoting bone ingrowth into the coating following implantation.

21. The implant recited in claim 20 further comprising a second surface coating on at least a portion of the first surface coating.

22. The implant recited in claim 1 wherein the body member is configured in cross section to inhibit rotational motion of the body member following implantation.

23. The implant recited in claim 22 wherein the body member is triangular in cross section.

24. The implant recited in claim 22 wherein the body member is fluted in cross section.

25. The implant recited in claim 22 wherein the body member is scalloped in cross section.

26. The implant recited in claim 1 wherein the body member is circular in cross section.

27. The implant of claim 1 wherein the distal end of the body member is closed.

* * * * *